US007691368B2

(12) United States Patent
Parisot et al.

(10) Patent No.: US 7,691,368 B2
(45) Date of Patent: *Apr. 6, 2010

(54) VACCINE FORMULATIONS

(75) Inventors: Alexis Guy Andre Parisot, Lyons (FR); Stephanie Marie-Catherine Desgouilles-Blechet, Lyons (FR); Catherine Charreyre, Saint-Laurent de Mure (FR); Claude Jean Marie Roulet, Vénissieux (FR)

(73) Assignee: Merial Limited, Duluth, GA (US)

( * ) Notice: Subject to any disclaimer, the term of this patent is extended or adjusted under 35 U.S.C. 154(b) by 689 days.

This patent is subject to a terminal disclaimer.

(21) Appl. No.: 11/107,000

(22) Filed: Apr. 15, 2005

(65) Prior Publication Data
US 2006/0233831 A1 Oct. 19, 2006

(51) Int. Cl.
*A01N 43/04* (2006.01)
*A01N 65/00* (2006.01)
*A61K 39/38* (2006.01)
(52) U.S. Cl. .................. 424/93.1; 424/184.1; 514/44 R
(58) Field of Classification Search ............... 424/184.1
See application file for complete search history.

(56) References Cited
U.S. PATENT DOCUMENTS
5,250,289 A 10/1993 Boothroyd et al.

7,371,395 B2 * 5/2008 Parisot et al. ............ 424/283.1

FOREIGN PATENT DOCUMENTS

| EP | 0782846 A2 | 7/1997 |
| PL | 155558 B1 * | 12/1991 |
| WO | WO2005009462 A2 | 2/2005 |

OTHER PUBLICATIONS

Hong (Biotechnology and Bioprocess Engineering vol. 12, pp. 73-79, 2007).*

* cited by examiner

*Primary Examiner*—Mark Navarro
(74) *Attorney, Agent, or Firm*—Judy Jarecki-Black; Thomas Kowalski, Esq.; Merial Limited

(57) ABSTRACT

The present invention relates to oil-in-water emulsions, their use as adjuvants, and pharmaceutical, immunologic, or vaccine compositions that may comprise the same. In one embodiment, the oil-in-water (O/W) emulsion may comprise an aqueous solution containing an immunogen, a mineral oil, a non-ionic lipophilic ethoxylated fatty alcohol and a non-ionic hydrophilic surfactant. In another embodiment, the oil-in-water (O/W) emulsion may comprise an aqueous solution containing an immunogen, a non-ionic lipophilic surfactant, a mineral oil and a non-ionic hydrophilic ethoxylated fatty alcohol. The present invention also encompasses a method of making a vaccine composition using the adjuvant of the instant invention, the vaccine composition so obtained and methods of use.

20 Claims, No Drawings

VACCINE FORMULATIONS

INCORPORATION BY REFERENCE

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to oil-in-water emulsions, their use as adjuvants, and pharmaceutical, immunologic, or vaccine compositions comprising the same.

BACKGROUND OF THE INVENTION

The use of adjuvants in vaccines is well known. An adjuvant is a compound that, when combined with a vaccine immunogen, increases the immune response to the vaccine immunogen. Among strategies that promote immunogenicity of a protein, glycoprotein or peptide are those that emulsify vaccine immunogens. (Nossal 1999, In: *Fundamental Immunology*. Paul (Ed.), Lippincott-Raven Publishers, Philadelphia, Pa.; Vogel and Powell, 1995, In: *Vaccine Design. The Subunit and Adjuvant Approach*. Powell and Newman (Eds.), Plenum Press, NY, N.Y. p. 141). Because of the essential role that adjuvants play in improving the immunogenicity of vaccine immunogens, the use of adjuvants in the formulation of vaccines has been virtually ubiquitous (Nossal, 1999, supra; Vogel and Powell, 1995, supra; the teachings of which are incorporated herein by reference). Conventional adjuvants, well-known in the art, are diverse in nature. They may, for example, consist of water-insoluble inorganic salts, liposomes, micelles or emulsions, i.e. Freund's adjuvant. Other adjuvants may be found in Vogel and Powell, 1995, mentioned supra. Although there is no single mechanism of adjuvant action, an essential characteristic is their ability to significantly increase the immune response to a vaccine immunogen as compared to the response induced by the vaccine immunogen alone (Nossal, 1999, supra; Vogel and Powell, 1995, supra). In this regard, some adjuvants are more effective at augmenting humoral immune responses; other adjuvants are more effective at increasing cell-mediated immune responses (Vogel and Powell, 1995, supra); and yet another group of adjuvants increase both humoral and cell-mediated immune responses against vaccine antigens (Vogel and Powell, 1995, supra).

Generally, emulsions used in vaccine formulation comprise a mixture of oil, aqueous solution and surfactants. Some emulsions incorporate a lipophilic surfactant such as Span 80® and a hydrophilic surfactant such as Tween 80®. These emulsions may also contain compounds such as lecithin or saponin known to have ionic surfactant properties.

However, problems of stability can be observed with emulsions used as vaccine adjuvants, in particular during storage or transport. Lipase or esterase enzymatic activities present in the solution or suspension of immunogen can hydrolyse the surfactants of the emulsion and can lead to a lack of stability of the adjuvant. The lipases or esterases can come for example from the cell culture used to grow viruses or from bacteria This is particularly true when these compositions contain concentrated immunogens, especially non-purified concentrated immunogens. Typically, this is the case with adjuvants used in inactivated (killed) vaccines. This problem is even more significant with multivalent vaccine compositions because the immunogens are more concentrated in the same volume of diluent.

Another problem with adjuvant use is linked to a risk of adverse events such as toxicity or local inflammation at the site of injection. For example, a local inflammatory response and/or granulomae may result after injection. In order to limit such an adverse reaction, surfactants and other components in the emulsion may be reduced; however, the reduction may then result in a decrease in the stability of the vaccine composition. There is, therefore, a need for novel adjuvants and vaccine compositions containing such adjuvants with increased safety and stability.

Citation or identification of any document in this application is not an admission that such document is available as prior art to the present invention.

SUMMARY OF THE INVENTION

In a first embodiment the present invention provides for a novel oil-in-water (O/W) emulsion, with increased stability in the presence of bacteria, parasites or viruses suspensions, especially those concentrated and non-purified or weakly purified.

Another embodiment of the present invention provides for a stable, safe and easily administrable, in particular injectable, O/W emulsion acting as a vehicle for the delivery of a pharmaceutical composition comprising at least one active ingredient that may be, more particularly, an immunogen.

Yet another embodiment of the present invention provides for a stable, safe and injectable O/W emulsion acting as an adjuvant to increase the immune response induced by an immunogen. In particular, the present invention provides a novel adjuvant which, when used in a vaccine composition containing an immunogen increases the vaccinate's cellular immune response, humoral immune response or, advantageously, both to the immunogen.

Yet another embodiment of the present invention provides a stable, safe and immunogenic composition or vaccine comprising an O/W emulsion.

A further embodiment of the present invention provides for a method of making a vaccine composition using the adjuvant of the instant invention; the vaccine composition so obtained; and methods of using thereof.

Still another embodiment of the present invention provides for a kit comprising an immunogen or other pharmaceutical product in a first vial, and an adjuvant made according to the present invention in a second vial, with the adjuvant designed to be mixed with the immunogen or other vaccine product before use.

In one embodiment, the present invention provides for an oil-in-water (O/W) emulsion that may comprise:

(1) an aqueous solution containing an immunogen;
(2) a mineral oil;
(3) a non-ionic lipophilic ethoxylated fatty alcohol;
(4) a non-ionic hydrophilic surfactant selected from the group of ethoxylated fatty alcohol, polyoxyethylene-polyoxypropylene block copolymer or any combination thereof.

In another embodiment, the present invention provides for an oil-in-water (O/W) emulsion that may comprise:

(1) an aqueous solution containing an immunogen;

(2) a non-ionic lipophilic surfactant selected from the group of ethoxylated fatty alcohol, polyoxyethylene-polyoxypropylene block copolymer or any combination thereof;

(3) a mineral oil;

(4) a non-ionic hydrophilic ethoxylated fatty alcohol.

The emulsions made according to the present invention are based on a combination of at least two surfactants chosen among the members of two different groups of surfactants (lipophilic and hydrophilic surfactants), and it is possible to use one or more surfactants pertaining to each group.

In yet another advantageous embodiment, the present invention provides for a vaccine composition comprising a novel emulsion that may contain at least one immunogen suitable for eliciting an immunologic response in a vaccinate. The invention further provides such compositions wherein the emulsion acts as an adjuvant to increase the immune response induced by the immunogen, in particular, to increase the cellular response, the humoral response or advantageously both.

In an advantageous embodiment, the antigen or immunogen is, or is derived from, *Mycoplasma*, advantageously *Mycoplasma hyopneumoniae*, porcine circovirus, advantageously porcine circovirus 2 or *Helicobacter*, advantageously *Helicobacter cerdo* or *Helicobacter pylori*.

In another advantageous embodiment the present invention provides for a method of making a vaccine composition wherein an immunogen, especially an immunogen in lyophilized form or in an aqueous solution, is mixed with the adjuvant according to the instant invention. The immunogen may be selected from the group consisting of: inactivated pathogens, attenuated pathogens, sub-unit antigens, recombinant expression vectors including plasmids, and the like. The pathogen may be bacterial, viral, protozoal, parasitic or fungal in origin or the immunogen may be an toxoid.

In another advantageous embodiment, the present invention provides for a method of inducing an immune response in a vaccinate against a pathogen comprising administering the vaccine composition of the present invention to the vaccinate.

In another advantageous embodiment, the present invention provides for kits comprising at least two vials, in a first vial an immunogen, especially an immunogen in lyophilized form or in solution in an aqueous medium, and in a second vial an adjuvant or emulsion according to the present invention.

It is noted that in this disclosure and particularly in the claims, terms such as "comprises", "comprised", "comprising" and the like can have the meaning attributed to such terms in U.S. Patent law; e.g., they can mean "includes", "included", "including", and the like; and that terms such as "consisting essentially of" and "consists essentially of" have the meaning ascribed to them by U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

For convenience, certain terms employed in the specification, examples, and appended paragraphs and claims are collected here.

As used herein, the term "animal" encompasses all vertebrate animals including humans. It also includes an individual animal in all stages of development, including embryonic and fetal stages. In particular, the term "vertebrate animal" includes, but not limited to, humans, canines (e.g., dogs), felines (e.g., cats); equines (e.g., horses), bovines (e.g., cattle) porcines (e.g., pigs) ovines (e.g. sheep), caprines (e.g. goats), rabbits as well as in avians. The term "avian" as used herein refers to any species or subspecies of the taxonomic class Aves, such as, but not limited to, chickens (breeders, broilers and layers), turkeys, ducks, a goose, a quail, pheasants, parrots, finches, hawks, crows and ratites including ostrich, emu and cassowary.

As used herein, the term "pig" or "piglet" pertains to an animal of porcine origin, while "sow" refers to a female of reproductive age and capability.

As used herein, the term "virulent" pertains to an isolate that retains its ability to be infectious in an animal host.

As used herein, the term "inactivated vaccine" encompasses a vaccine composition containing an infectious organism or pathogen that is no longer capable of replication or growth. The pathogen may be bacterial, viral, protozoal, parasitic or fungal in origin. Inactivation may be accomplished by a variety of methods including high pressure, chemical treatment (for example, treatment with thimerosal or formalin), sonication, radiation, heat or any other conventional means sufficient to prevent replication or growth of the organism while maintaining its immunogenicity.

As used herein, the term "immunogenicity" means capable of producing an immune response in a host animal against an immunogen or immunogens. This immune response forms the basis of the protective immunity elicited by a vaccine against a specific infectious organism.

As used herein, the term "immune response" refers to a response elicited in an animal. An immune response may refer to cellular immunity (CMI); humoral immunity or may involve both. The present invention also contemplates a response limited to a part of the immune system. For example, a vaccine composition of the present invention may specifically induce an increased gamma interferon response.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a glycoprotein, a lipoprotein, a polypeptide, a peptide, an epitope, a hapten, or any combination thereof. Alternately, the immunogen or antigen may comprise a toxin or antitoxin.

As used herein, the term "multivalent" means a vaccine containing more than one antigen whether from the same species (e.g., different isolates of *Mycoplasma hyopneumoniae*), from a different species (e.g., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

As used herein, the term "adjuvant" means a substance added to a vaccine to increase a vaccine's immunogenicity.

The mechanism of how an adjuvant operates is poorly understood. Some adjuvants are believed to enhance the immune response by slowly releasing the antigen, while other adjuvants can mediate their effects by any of the following mechanisms: increasing cellular infiltration, inflammation, and trafficking to the injection site, particularly for antigen-presenting cells (APC); promoting the activation state of APCs by upregulating costimulatory signals or major histocompatibility complex (MHC) expression; enhancing antigen presentation; or inducing cytokine release for indirect effect. The most appropriate adjuvant for a given vaccine immunogen will depend to a large extend on the type of immune response that is required for protective immunity. The adjuvant selection may be somewhat empirical. Known vaccine adjuvants include, but are not limited to, oil and water emulsions (for example, complete Freund's adjuvant and incomplete Freund's adjuvant), in particular oil-in-water emulsions, water-in-oil emulsions, water-in-oil-in-water emulsions. They include also for example saponin, aluminum hydroxide, dextran sulfate, carbomer, sodium alginate, "AVRIDINE" (N, N-dioctadecyl-N',N'-bis(2-hydroxyethyl)-propanediamine), paraffin oil, muramyl dipeptide, cationic lipids (e.g., DMRIE, DOPE and combinations thereof) and the like.

As used herein, the terms "pharmaceutically acceptable carrier" and "pharmaceutically acceptable vehicle" are interchangeable and refer to a fluid vehicle for containing vaccine immunogens that can be injected into a host without significant adverse effects. Suitable pharmaceutically acceptable carriers known in the art include, but are not limited to, sterile water, saline, glucose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like. The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Doses and dose volumes are herein discussed in the general description and can also be determined by the skilled artisan from this disclosure read in conjunction with the knowledge in the art, without any undue experimentation.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, ocular) or via a parenteral route (e.g. intradermal, intramuscular, subcutaneous). For the parenteral administration of the product to the host, either a syringe with a needle or a needlefree injector can be used. Vaccine compositions can be administered alone, or can be co-administered or sequentially administered with other treatments or therapies. Forms of administration may include suspensions and preparations for parenteral, subcutaneous, intradermal or intramuscular administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

The present invention provides in one embodiment a novel oil-in-water (O/W) adjuvant or emulsion which may comprise:
(1) an aqueous solution containing a vaccine antigen or immunogen capable of inducing an immune response in a host;
(2) a non-ionic lipophilic ethoxylated fatty alcohol;
(3) a mineral oil;
(4) a non-ionic hydrophilic surfactant selected from the group of ethoxylated fatty alcohol, polyoxyethylene-polyoxypropylene block copolymer and/or any combination thereof.

The present invention provides in another embodiment a novel oil-in-water (O/W) adjuvant or emulsion that may comprise:
(1) an aqueous solution containing a vaccine antigen or immunogen capable of inducing an immune response in a host;
(2) a non-ionic lipophilic surfactant selected from the group of ethoxylated fatty alcohol, polyoxyethylene-polyoxypropylene block copolymer and/or any combination thereof;
(3) a mineral oil;
(4) a non-ionic hydrophilic ethoxylated fatty alcohol.

The emulsions made according to the present invention are based on a combination of at least two surfactants chosen among the members of two different groups of surfactants (lipophilic and hydrophilic surfactants), and it is possible to use one or more surfactant pertaining to each group.

A lipophilic ethoxylated fatty alcohol can be an ethoxylated fatty alcohol which may comprise about 43% of the molecular weight (w/w) or less of ethylene oxide (EO). A lipophilic polyoxyethylene-polyoxypropylene block copolymer (POE-POP block copolymer) is a copolymer which may comprise about 35% (w/w) or less of ethylene oxide.

A hydrophilic ethoxylated fatty alcohol can be an ethoxylated fatty alcohol comprising more than about 43% (w/w) of ethylene oxide (EO). A hydrophilic POE-POP block copolymer is a copolymer comprising about 55% (w/w) or more of ethylene oxide.

For the non-ionic hydrophilic surfactants the fatty alcohol can be a C9 to C22 fatty alcohol and advantageously selected from the group consisting of an oleyl, cetyl, stearyl, isostearyl, lauryl alcohol, and combinations thereof, advantageously an oleyl alcohol and more advantageously an oleyl alcohol with 5 to 21 EO. The POE-POP block copolymer has a MW of about 3000 to about 16000.

The group of non-ionic hydrophilic surfactants includes, but is not limited to, the ethoxylated fatty alcohols: Brij® 76 [Steareth-10], Brij® 56 [Ceteth-10], Brij® 96/97 [Oleth-10], Brij® 98 [Oleth-20], Brij® 721 [Steareth-21], Brij® 58 [Ceteth-20], Brij® 35 [Laureth-23], Brij® 78 [Steareth-20], (Uniqema) Volpo® N5 [Oleth-5], Volpo® CS6 [Ceteareth-6], Volpo® CS12 [Ceteareth-12], Volpo® CS20 [Ceteareth-20], Volpo® CS25 [Ceteareth-25], Volpo® CS23 [Ceteareth-23] (Croda), BL9-EX [Laureth-9], BC-7 [Ceteth-7], BT-5 [C12-14 Pareth-5], BT-7 [C12-14 Pareth-7], BT-9 [C12-14 Pareth-9], BT-12 [C12-14 Pareth-12], BD-10 [C12-15 Pareth-10], BO-7V [Oleth-7], BC5.5 [Ceteht-6], BL-21 [Laureth-21], BL-25 [Laureth-25], BC-15TX [Ceteth-15], BC-23 [Ceteth- 23], BC-25TX [Ceteth-25], BO-15V [Oleth-15], BO-50V [Oleth-50], BB-20 [Beheneth-20], (Nikko Chemicals), and combinations thereof, to the POE-POP block copolymers: Lutrol® F127 [Poloxamer 407], Lutrol® F68 [Poloxamer 188], Lutrol® F108 [Poloxamer 338], Lutrol® F98 [Poloxamer 278], Lutrol®F87 [Poloxamer 227], Lutrol® F88 [Poloxamer 228], Lutrol® F77 [Poloxamer 207], Lutrol® F38 [Poloxamer 108] (BASF), Tetronics®T1307, Tetronics®T1107, Tetronics®T908 (BASF), and combinations thereof.

For the non-ionic lipophilic surfactants, the fatty alcohol is a C9 to C22 fatty alcohol and advantageously selected from the group consisting of oleyl, cetyl, stearyl, isostearyl, lauryl alcohol and combinations thereof, advantageously an oleyl alcohol, more advantageously an ethoxylated oleyl alcohol with 1 to 4 EO. The POE-POP block copolymer has a MW of about 1000 to about 8000.

The group of non-ionic lipophilic surfactants includes, but is not limited to, the ethoxylated fatty alcohols: Brij® 30 [Laureth-4], Brij® 92/93 [Oleth-2], Brij® 72 [Steareth-2], Brij® 52 [Ceteth-2] (Uniqema), Volpo® L3 [C12-13 Pareth-3], Volpo® N3 [Oleth-3], Volpo® L4 [C12-13 Pareth-4] (Croda), BS-4 [Steareth-4], BD-2 [C12-15 Pareth-2], BD-4 [C12-15 Pareth-4], BT-3 [C12-14 Pareth-3] (Nikko Chemicals) and combinations thereof, to the POE-POP block copolymers: Pluronic® L121 [Poloxamer 401], Pluronic® L101 [Poloxamer 331], Pluronic® L81 [Poloxamer 221], Pluronic® L62 [Poloxamer 182], Pluronic® L43 [Poloxamer 123], Pluronic® P103 [Poloxamer 333], Pluronic® L123 [Poloxamer 403], Lutrol® L63 [Poloxamer 183], Lutrol® P122 [Poloxamer 402], Lutrol® L92 [Poloxamer 272], Lutrol® L72 [Poloxamer 202], Lutrol® L42 [Poloxamer 122], Lutrol® L61 [Poloxamer 181] (BASF), Tetronics®T1301, Tetronics®T701, Tetronics®T901 (BASF), and combinations thereof.

The surfactants of the invention may have fatty alcohol from animal or vegetable origin. The change of one origin for the other could be done simply with only minor adjustment in the formulation of the emulsion.

An emulsion according to the invention may have an overall concentration of surfactants, by weight per volume of emulsion, from about 0.2% to about 6.5%, in particular from about 1% to about 6%, advantageously from about 1.5% to about 5%, more advantageously from about 2% to about 3%.

Such emulsions have a low viscosity and are easily injectable.

In an advantageous embodiment, the present invention provides for an oil-in-water (O/W) emulsion which may comprise:
 (1) an aqueous solution containing a vaccine antigen or immunogen capable of inducing an immune response in a host;
 (2) a non-ionic lipophilic ethoxylated fatty alcohol;
 (3) a mineral oil;
 (4) a non-ionic hydrophilic ethoxylated fatty alcohol comprising more than about 43% and less than about 71% (w/w) of ethylene oxide;
 (5) a non-ionic hydrophilic ethoxylated fatty alcohol comprising about 71% or more (w/w) of ethylene oxide.

The ethoxylated fatty alcohol comprising more than about 43% and less than about 71% (w/w) of ethylene oxide is advantageously an ethoxylated oleyl alcohol with 5 to 14 EO. The fatty alcohol comprising about 71% or more (w/w) of ethylene oxide is advantageously an ethoxylated oleyl alcohol with 15 EO or more.

In this advantageous embodiment, the concentration of non-ionic hydrophilic ethoxylated fatty alcohol is generally from about 1.0% to about 5.0%, in particular from about 1.5% to about 4.5%, more advantageously from about 2.0% to about 3.5%, expressed as a percentage in weight by volume of emulsion (w/v). For the non-ionic highly hydrophilic ethoxylated fatty alcohol the concentration is generally from about 0.01% to about 3.0%, particularly from about 0.05% to about 2.5%, more advantageously from about 0.1% to about 2.0% (w/v). The concentration of the non-ionic lipophilic ethoxylated fatty alcohol is generally from about 0.1% to about 2.5%, in particular from about 0.2% to about 2.0%, advantageously from about 0.2% to about 1.5%, more advantageously from about 0.2% to about 1.2% (w/v).

In an advantageous embodiment, the present invention provides for an oil-in-water (O/W) emulsion which may comprise:
 (1) an aqueous solution containing a vaccine antigen or immunogen capable of inducing an immune response in a host;
 (2) a non-ionic lipophilic ethoxylated fatty alcohol;
 (3) a mineral oil;
 (4) a non-ionic hydrophilic ethoxylated fatty alcohol;
 (5) a non-ionic hydrophilic polyoxyethylene-polyoxypropylene block copolymer.

The hydrophilic ethoxylated fatty alcohol is advantageously a fatty alcohol comprising more than about 43% and less than about 71% (w/w) of ethylene oxide, and more advantageously an ethoxylated oleyl alcohol with 5 to 14 EO. The non-ionic POE-POP block copolymer may advantageously comprise 70% (w/w) or more of ethylene oxide.

In this advantageous embodiment, the concentration of non-ionic hydrophilic ethoxylated fatty alcohol is generally from about 1.0% to about 5.0%, in particular from about 1.5% to about 4.5%, more advantageously from about 2.0% to about 3.5%, expressed as a percentage in weight by volume of emulsion (w/v). For the non-ionic POE-POP block-copolymer the concentration is generally from about 0.01% to about 2.0%, more particularly from about 0.1% to about 1.5% (w/v). The concentration of the non-ionic lipophilic ethoxylated fatty alcohol is generally from about 0.1% to about 2.5%, in particular from about 0.2% to about 2.0%, advantageously from about 0.2% to about 1.5%, more advantageously from about 0.2% to about 1.2% (w/v).

Generally, the emulsion according to the invention may have a phase inversion temperature (PIT), which is $\geq 25°$ C., in particular ranges from about 28° C. to about 65° C., more particularly from about 33° C. to about 60° C.

The PIT is the temperature at which a water-in-oil emulsion changes to an oil-in-water emulsion or de-phases (breaks of the emulsion and separation of the 2 phases). The PIT value may be measured by various means, for example by visual appearance or by conductivity. The emulsion is placed at a temperature below the PIT of the emulsion, for example of about 25° C. in a water-bath. The temperature is progressively increased. The change of the visual aspect of the emulsion is observed in comparison with a control emulsion, notably the fluidity, the separation in two phases, the change of the surface aspect due to the migration of the oily phase to the surface. The temperature, for which this change of visual aspect was observed, is the PIT value of the emulsion. Alternatively, the PIT is determined by the quick passage from a conductivity value of about 5-15 milliSiemens/centimeter (mS/cm) (oil-in-water emulsion) to a value of about 0 mS/cm (water-in-oil emulsion), for physiological saline as aqueous phase, measured by a probe placed into the emulsion, near its surface. The temperature, for which the transition was observed, is the PIT value of the emulsion. One of ordinary skill in the art will be able to determine combinations of surfactants and oil, including their respective concentrations, in order to produce emulsions according to the invention, and in particular emulsions having a PIT value within the ranges defined above without undue experimentation.

Generally, emulsions according to the present invention may contain, by volume per volume (v/v) of emulsion, from about 2% to about 50% of oil phase including the oil(s) and the surfactants, in particular from about 4% to about 40%, advantageously from about 8% to about 35% and, more advantageously, from about 15% to about 30% of oil phase. By definition, ranges of values in the present specification include always the limit of the range, unless otherwise indicated.

The oil used may be a mineral oil including, but not limited to, paraffin oil such as isoparaffinic oil and/or naphthenic oil, squalane, squalene, pristane, polyisobutene, hydrogenated polyisobutene, polydecene, polyisoprene, polyisopropene and the like. One advantageous mineral oil useful in the present invention may include an oil comprising a linear or ramified carbon chain having a number of carbon atoms greater than 15, advantageously from 15 to 32, and free of aromatic compounds. Such oils may, for example, be those marketed under the name MARCOL® 52 or MARCOL® 82 (Esso) or "DRAKEOL® 6VR" (Penreco).

The oil may also be a mixture of oils comprising at least 2 oils selected among the oils described herein, and in any proportion. The mixture of oils may also comprise at least one oil selected among the oils described above and at least one vegetable oil, and this vegetable oil represents from about 0.1% to about 33% of the oily phase, advantageously from about 5% to about 15% v/v. These vegetable oils are unsaturated oils rich in oleic acid that are biodegradable and advantageously liquid at the storage temperature (about +4 degree C.) or at least make it possible to give emulsions that are liquid at this temperature. For example the vegetable oil may be groundnut oil, nut oil, sunflower oil, safflower oil, soya oil, evening primrose oil and the like.

Generally, the present invention envisions using an aqueous solution comprising a suitable veterinary or pharmaceutically acceptable vehicle, excipient, or diluent including, but not limited to, sterile water, physiological saline, glucose, buffer and the like. The vehicle, excipient or diluent may also include polyols, glucids or pH buffering agents. The vehicle, excipient or diluent may, for example, also comprise amino acids, peptides, antioxidants, bactericide, bacteriostatic compounds. The aqueous solution is added to the oil and the surfactants in quantity to obtain 100% of the volume of the emulsion according to the invention.

The present invention contemplates an emulsion comprising a paraffin oil; an ethoxylated oleyl alcohol with 2-3 EO as non-ionic lipophilic surfactant; an ethoxylated oleyl alcohol with 5-6 EO as non-ionic hydrophilic surfactant; and a POE-POP block copolymer with approximately 70 to 80% EO and a MW around 9800 to 16000 as non-ionic hydrophilic surfactant. In particular the paraffin oil is at a concentration from about 5% about 50% and advantageously from about 15% to about 30% (v/v); the ethoxylated oleyl alcohol with 2-3 EO is at the concentration from 0.1% to 1.5%, advantageously from 0.1% to 1.2% (w/v); the ethoxylated oleyl alcohol with 5-6 EO is at the concentration from 1% to 5%, advantageously from 1% to 4% (w/v); and the POE-POP block copolymer with approximately 70 to 80% EO and a MW around 9800 to 16000 is at the concentration from 0.01% to 2%, advantageously from 0.05% to 1.5% (w/v).

In a second embodiment according to the present invention, the emulsion comprises a paraffin oil, an ethoxylated oleyl alcohol with 2-3 EO as non-ionic lipophilic surfactant; an ethoxylated oleyl alcohol with 10 OE as non-ionic hydrophilic surfactant; and a POE-POP block copolymer with approximately 70 to 80% EO and a MW around 9800 to 16000 as non-ionic hydrophilic surfactant. In particular the paraffin oil is at a concentration from 5% to 50%, advantageously from 15% to 30% (v/v); the ethoxylated oleyl alcohol with 2-3 EO is at the concentration from 0.2% to 3%, advantageously from 0.5% to 3% (w/v); the ethoxylated oleyl alcohol with 10 EO is at the concentration from 0.2% to 3%, advantageously from 0.5% to 3% (w/v); and the POE-POP block copolymer with approximately 70 to 80% EO and a MW around 9800 to 16000 is at the concentration from 0.01% to 2%, advantageously from 0.05% to 1.5% (w/v).

In a third embodiment according to the present invention, the emulsion comprises a paraffin oil, an ethoxylated oleyl alcohol with 2-3 EO as non-ionic lipophilic surfactant and an ethoxylated oleyl alcohol with 5-6 OE as non-ionic hydrophilic surfactant. In particular the paraffin oil is at a concentration from 5% to 50%, advantageously from 15% to 35% (v/v); the ethoxylated oleyl alcohol with 2-3 EO is at the concentration from 0.1% to 3%, advantageously from 0.5% to 2% (w/v); the ethoxylated oleyl alcohol with 5-6 EO is at the concentration from 1% to 5%, advantageously from 2.0% to 4.5% (w/v).

Optionally other compounds may be added as co-adjuvants to the emulsion, including, but not limited to, aluminum; CpG oligonucleotides (ODN), in particular ODN 2006, 2007, 2059, 2216 or 2135 (Pontarollo R. A. et al., *Vet. Immunol. Immunopath*, 2002, 84: 43-59; Wernette C. M. et al., *Vet. Immunol. Immunopath*, 2002, 84: 223-236; Mutwiri G. et al., *Vet. Immunol. Immunopath*, 2003, 91: 89-103; Kerkmann M. et al., *J. Immunol.*, 2003, 170: 4465-4474); polyA-polyU ("Vaccine Design The Subunit and Adjuvant Approach", edited by Michael F. Powell and Mark J. Newman, *Pharmaceutical Biotechnology*, 6: 03); dimethyldioctadecylammonium bromide (DDA) ("Vaccine Design: The Subunit and Adjuvant Approach", edited by Michael F. Powell and Mark J. Newman, *Pharmaceutical Biotechnology*, volume 6: 157), N,N-dioctadecyl-N',N'-bis(2-hydroxyethyl)propanediamine (such as Avridine®) (*Ibid*, p. 148), carbomer, chitosan (see U.S. Pat. No. 5,980,912 for example).

The present invention also provides a method of making a vaccine composition or immunologic composition comprising at least one antigen or immunogen and an adjuvant or emulsion made according to the present invention. The immunogen may be incorporated during emulsion formation or, in an alternate embodiment, the immunogen may be added to the emulsion later as, for example, just before use.

The entire amount of the aqueous solution used may be present in the emulsion first produced. Or it may be that only a part of this aqueous solution is used to form the emulsion, and the remaining quantity of aqueous solution is added with incorporation of the immunogen. The immunogen or antigen may be in a lyophilized form or present in some other appropriate solid form and then mixed with the emulsion or, alternately, the antigen may be in solution, in particular in an aqueous solution, and this solution mixed with the emulsion.

Surfactants are advantageously added to either the oil or the aqueous solution according to their solubility. For example, the non-ionic lipophilic surfactants are added to the oil according to the invention while non-ionic hydrophilic surfactants are added to the aqueous solution.

The emulsification can be prepared according to conventional methods known to one of ordinary skill in the art. For example, in one embodiment of the present invention, the emulsion can be prepared at a temperature below the PIT of the emulsion, in particular at room temperature, e.g. at about 30° C. The aqueous phase and the oily phase are mixed together by a mechanical agitation, e.g. with a turbine equipped with a rotor-stator able to create a high shearing force. Advantageously, the agitation starts at a low rotation speed and slowly increases in relation to the progressive addition generally of the aqueous solution in the oil. Advantageously the aqueous solution is progressively added to the oil. The ratio of oil/aqueous solution may be adapted to obtain a water-in oil (W/O) emulsion, for example, at a concentration of about 40% to about 55% of oil (v/v). When the agitation is stopped, the emulsion changes progressively to an O/W emulsion while cooling at room temperature (phase inversion). After inversion and if needed, the emulsion is diluted by addition of an aqueous solution to obtain the desired concentration of oil into the final emulsion. The emulsion may be stored at about 5° C.

In another embodiment, the emulsion can be prepared at a temperature higher than the PIT of the emulsion. In a first step, the aqueous phase and the oily phase are mixed together at a temperature higher than the PIT of the emulsion. Advantageously the aqueous solution is progressively added to the oil. The ratio of oil/aqueous solution may be adapted to obtain a water-in oil (W/O) emulsion, for example at a concentration of about 40% to about 55% of oil (v/v). The emulsification may be done by an agitation with low or no shearing force, e.g. with a static mixer or a marine helix (propeller) or with a turbine at a very low rotation speed. The emulsion obtained is a water-in-oil (W/O) emulsion. In a second step, the emulsion is cooled progressively below the PIT. During this step, the emulsion changes to an O/W emulsion (phases inversion). After inversion and if needed, the emulsion is diluted by addition of an aqueous solution to obtain the desired concentration of oil into the final emulsion. The emulsion may be stored at about 5° C.

The size of the oil droplets in the emulsion may be from about 100 nm to about 500 nm. The emulsion may be used, for example, as an adjuvant to formulate a vaccine composition or a pharmaceutical composition. The emulsion may also be used as a solvent to dissolve a dried product, especially a lyophilised product containing, for example, attenuated microorganisms or live recombinant vectors.

In a particular embodiment, a pre-emulsion is produced with only a part of the aqueous solution. This pre-emulsion may be diluted by addition of a suspension of an active ingredient such as a drug or an immunogen, advantageously an immunogen, to obtain the final composition. Alternatively, the pre-emulsion may be diluted with an aqueous solution and used to dissolve a dried product such as a lyophilised product.

The immunogen or antigen suitable for use in the present invention may be selected from the group consisting of inactivated pathogens, attenuated pathogens, immunogenic subunits (e.g. proteins, polypeptides, peptides, epitopes, haptens), or recombinant expression vectors, including plasmids having immunogenic inserts. In one embodiment of the present invention, the immunogen is an inactivated or killed microorganism. In another embodiment of the invention, the vaccine composition comprises an immunogen selected from the group of avian pathogens including, but not limited to, *Salmonella typhimurium, Salmonella enteritidis*, Infectious Bronchitis virus (IBV), Newcastle Disease virus (NDV), egg drop syndrome virus (EDS), or Infectious Bursal Disease virus (IBDV), avian influenza virus, and the like, and combinations thereof.

Alternately, the vaccine composition comprises an immunogen selected from a feline pathogen such as, but not limited to, feline herpesvirus (FHV), feline calicivirus (FCV), feline leukemia virus (FeLV), feline immunodeficiency virus (FIV), rabies virus, and the like, and combinations thereof.

In yet another embodiment, a vaccine composition of the present invention comprises an immunogen selected from a canine pathogen including, but not limited to, rabies virus, canine herpesvirus (CHV), canine parvovirus (CPV), canine coronavirus, *Leptospira canicola, Leptospira icterohaemorragiae, Leptospira grippotyphosa, Borrelia burgdorferi, Bordetella bronchiseptica* and the like, and combinations thereof.

In yet another embodiment of the invention the composition comprises an immunogen selected from an equine pathogen, such as equine herpesvirus (type 1 or type 4), equine influenza virus, tetanus, West Nile virus, and the like and/or combinations thereof.

In yet another embodiment of the invention, the composition comprises an immunogen selected from an bovine pathogen, such as rabies virus, bovine rotavirus, bovine parainfluenza virus type 3 (bPIV-3), bovine coronavirus, bovine viral diarrhea virus (BVDV), foot and mouth disease virus (FMDV), bovine respiratory syncytial virus (BRSV), Infectious Bovine Rhinotracheitis virus (IBR), *Escherichia coli, Pasteurella multocida, Pasteurella haemolytica* and the like and combinations thereof.

In still another embodiment of the present invention, the composition comprises an immunogen selected from a porcine pathogen such as, but not limited to, swine influenza virus (SIV), porcine circovirus type 2 (PCV-2), porcine reproductive respiratory syndrome virus (PRRS), pseudorabies virus (PRV), porcine parvovirus (PPV), FMDV, hog cholera (HCV), *Mycoplasma hyopneumoniae, Erysipelothrix rhusiopathiae, Pasteurella multocida, Bordetella bronchiseptica, Escherichia coli, Helicobacter cerdo. Helicobacter pylori* and the like, and combinations thereof.

An advantageous embodiment of the invention provides for vaccine compositions comprising at least one immunogen and an emulsion in a pharmaceutically acceptable vehicle. Immunogens comprising viruses, bacteria, fungi and the like may be produced by in vitro culture methods using appropriate culture medium or host cells lines and conventional methods well known to those of ordinary skill in the art. For example, PRRS may be cultured in an appropriate cell line, such as MA-104 cell line (see U.S. Pat. Nos. 5,587,164; 5,866,401; 5,840,563; 6,251,404 among others). In a similar manner, PCV-2 may be cultured using PK-15 cells line (see U.S. Pat. No. 6,391,314); SIV may be cultured on eggs (U.S. Pat. No. 6,048,537); and *Mycoplasma hyopneumoniae* may be cultured in a appropriate culture medium (U.S. Pat. No. 5,968,525; U.S. Pat. No. 5,338,543; Ross R. F. et al., *Am. J Vet. Res.*, 1984, 45: 1899-1905).

To obtain an inactivated immunologic, or vaccine composition, the pathogen is advantageously inactivated after harvesting and, optionally, subjected to clarification by means of a chemical treatment using, for example, formaldehyde, beta-propiolactone, ethylenimine, binary ethylenimine (BEI), thimerosal, and the like, and/or a physical treatment (e.g. a heat treatment or sonication). Methods for inactivation are well known to those of skill in the art. For example, the PRRS virus may be inactivated by beta-propiolactone treatment (Plana-Duran et al., *Vet. Microbiol.*, 1997, 55: 361-370) or by BEI treatment (U.S. Pat. No. 5,587,164); inactivation of PCV-2 virus may be accomplished using ethyleneimine treatment or by beta-propiolactone treatment (U.S. Pat. No. 6,391, 314); swine influenza virus may be inactivated using a detergent like Triton, or with formaldehyde treatment (U.S. Pat. No. 6,048,537); *Mycoplasma hyopneumoniae* bacterium may be inactivated by formaldehyde treatment (Ross R. F. supra), by ethylenimine or BEI treatment (see WO 91/18627), or by thimerosal treatment (U.S. Pat. Nos. 5,968,525 and 5,338, 543).

The inactivated pathogen can be concentrated by conventional concentration techniques, in particular by ultrafiltration, and/or purified by conventional purification means, in particular using chromatography techniques including, but not limited to gel-filtration, ultracentrifugation on a sucrose gradient, or selective precipitations, in particular using a polyethylene glycol (PEG).

Immunogens useful in vaccine compositions according to the present invention also include expression vectors. A "vector" refers to a recombinant DNA or RNA plasmid or virus, e.g. poxviruses, adenoviruses, herpesviruses, that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors for translation of a polynucleotide encoding sequence. Also included are viral vectors.

The term "recombinant" means a polynucleotide of genomic cDNA, semisynthetic, or synthetic origin which either does not occur in nature or is linked to another polynucleotide in an arrangement not found in nature.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods and formulated in an emulsion according to the present invention.

The present invention also encompasses the formulation of multivalent immunological compositions or combination vaccine compositions. For example, antigens useful in a combination bovine bacterin made according to the present invention include, but are not limited to, *Mycoplasma bovis*, *Pasteurella* sp., particularly *P. multocida* and *P. haemolytica*, *Haemophilus* sp., particularly *H. somnus*, *Clostridium* sp., *Salmonella*, *Corynebacterium*, *Streptococcus*, *Staphylococcus*, *Moraxella*, *E. coli* and the like.

The present invention further provides for methods for inducing an immune response in a host, e.g., an animal, comprising administering to the host an immunological composition or a vaccine composition according to the invention. The immune responses elicited in this manner are notably antibody and/or cellular immune responses, and in particular, a gamma-interferon response.

In particular, the present invention provides for methods to immunize against, or to prevent or to reduce the symptoms caused by, infection of an animal with a pathogenic organism (for example, infection by a virus, bacteria, fungus, or protozoan parasite). The method of the present invention is useful in vertebrate animals including, but not limited to, humans, canine (e.g., dogs), feline (e.g., cats); equine (e.g., horses), bovine (e.g., cattle), ovine (e.g. sheep), caprine (e.g. goat) porcine animals (e.g., pigs) and rabbit, as well as in avians including, but not limited to, chickens, turkeys, ducks, geese, a quail, a pheasant, parrots, finches, hawks, crows and ratites (ostrich, emu, cassowary, and the like).

In a particular aspect of the invention, these methods consist of the vaccination of pregnant females before parturition by administering a vaccine composition made according to the invention. These methods further include the induction of protective antibodies elicited by the vaccination protocol and the transfer of these protective antibodies from vaccinated pregnant females to their offspring. The transfer of such maternal antibodies subsequently protects the offspring from disease.

The dosage of the vaccine composition made according to the present invention will depend on the species, breed, age, size, vaccination history, and health status of the animal to be vaccinated. Other factors like antigen concentration, additional vaccine components, and route of administration (i.e., subcutaneous, intradermal, oral, or intramuscular administration) will also impact the effective dosage. The dosage of vaccine to administer is easily determinable based on the antigen concentration of the vaccine, the route of administration, and the age and condition of the animal to be vaccinated. Alternatively, methodical immunogenicity trials of different dosages, as well as $LD_{50}$ studies and other screening procedures can be used to determine effective dosage for a vaccine composition in accordance with the present invention without undue experimentation. From the examples presented below, it will be readily apparent what approximate dosage and what approximate volume would be appropriate for using the vaccine composition described herein. The critical factor is that the dosage provides at least a partial protective effect against natural infection, as evidenced by a reduction in the mortality and morbidity associated with natural infection. The appropriate volume is likewise easily ascertained by one of ordinary skill in the art. For example, in avian species the volume of a dose may be from about 0.1 ml to about 0.5 ml and, advantageously, from about 0.3 ml to about 0.5 ml. For feline, canine and equine species, the volume of a dose may be from about 0.2 ml to about 3.0 ml, advantageously from about 0.3 ml to about 2.0 ml, and more advantageously, from about 0.5 ml to about 1.0 ml. For bovine and porcine species, the volume of dose may be from about 0.2 ml to about 5.0 ml, advantageously from about 0.3 ml to about 3.0 ml, and more advantageously from 0.5 ml to about 2.0 ml.

Repeated vaccinations may be advantageous at periodic time intervals to enhance the immune response initially or when a long period of time has elapsed since the last dose. In one embodiment of the present invention, the vaccine composition is administered as a parenteral injection (i.e., subcutaneously, intradermally, or intramuscularly). The composition may be administered as one dose or, in alternate embodiments, administered in repeated doses of from about two to about five doses given at intervals of about two to about six weeks, advantageously from about two to about five weeks. However, one of skill in the art will recognize that the number of doses and the time interval between vaccinations depends on a number of factors including, but not limited to, the age of the animal vaccinated; the condition of the animal, in particular in presence of maternal antibodies; the route of immunization; amount of antigen available per dose; and the like. For initial vaccination, the period will generally be longer than a week and advantageously will be between about two to about five weeks. For previously vaccinated animals, a booster vaccination, before or during pregnancy, at about an annual interval may be performed.

The present invention also contemplates administering a vaccine composition using a needlefree injector such as, but not limited to, Pigjet®, Avijet®, Dermojet® or Biojector® (Bioject, Oregon, USA). An person of ordinary skill in the art is able to adjust the specifications of the injector as required with regard to factors such as the species of the animal to be vaccinated; the age and weight of the animal, and the like without undue experimentation.

In one embodiment of the present invention, the method comprises a single administration of a vaccine composition formulated with an emulsion according to the invention. For example, in one embodiment, the vaccine composition is an inactivated *Mycoplasma hyopneumoniae* vaccine, while an alternate embodiment provides for a vaccine comprising an inactivated PCV2 virus composition. Other immunological compositions or vaccines are suitable for use in a single dose regimen including, but not limited to, inactivated PRRS and SIV. The vaccine may be administered also in presence of pre-existing antibodies.

The invention further relates to methods to treat a host, e.g., an animal, comprising administering to the host a pharmaceutical composition made according to the invention and comprising at least one immunogen selected from the group consisting of proteins or peptides, antibodies, allergens, CpG ODN, growth factors, cytokines, or antibiotics, and in particular CpG ODN or cytokines. These pharmaceutical compositions can be used to improve growth performances in an animal such as a chicken, a pig, or a cow.

The present invention further relates to a kit comprising a first vial containing an ingredient such as an immunogen or pharmaceutical composition and, in a second vial, an emulsion made according to the present invention. The immunogen may be in a lyophilized form, a dried form or in aqueous solution as described herein.

The invention will now be further described by way of the following non-limiting examples.

EXAMPLES

Example 1

Emulsion Manufacturing Method

The emulsion is produced in two steps as described as follows:

First Step: A high shear rotor-stator Silverson emulsifier (L4RT type with a disintegrating head with a diameter of 10 mm) was used to produce the formulations. To produce an emulsion, one volume of oily phase was emulsified at 35° C. with one volume of aqueous phase #1. The aqueous phase was added to the oily phase under agitation, 5000 rpm (rotation per minute) for 1 minute. The rotation speed was progressively increased with the augmentation of the volume to 8300 rpm during 1 minute. During this step the emulsion was a water-in-oil emulsion. The final LR4 emulsion is a O/W containing 20% oily phase. For the LR4 emulsion, phase composition was as follows:

| Oily phase (72 ml): | |
|---|---|
| Oleth-2 (Brij ® 92) | 1.8% w/v, |
| Oleth-5 (Volpo ® N5) | 8.2% w/v, |
| Paraffin oil (Marcol 82 ®) | 87.5% v/v, |
| Preservative | 2.5% v/v |

| Aqueous phase #1 (108 ml): | |
|---|---|
| Poloxamer 407 (Lutrol ® F127) | 0.58% w/v, |
| Isotonic buffer containing disodium and monopotassium phosphate 0.02 M (pH 7.8) | Q.S. to 100.0% v/v |

A 5% (w/v) solution of Lutrol® F127 in the same buffer as the vaccine, for example, in isotonic buffer containing disodium and monopotassium phosphate 0.02 M (pH 7.8) was used to prepare the aqueous phase #1.

When the agitation stopped, the emulsion changed to an oil-in-water emulsion. The emulsion was placed in a cold chamber at 5° C. for at least 4 hours. At this stage, the emulsion was a pre-emulsion containing 40% of oily phase.

Second Step: The aqueous phase #2 was prepared with 180 ml of disodium and monopotassium phosphate 0.02 M isotonic buffer pH 7.8 with the immunogen(s) (inactivated *Mycoplasma hyopneumoniae* immunogen, or PCV-2 immunogen, as described infra). The pre-emulsion as prepared in the first step was cooled to about 5° C., diluted by adding the same volume of the aqueous phase #2 at the same temperature, and mixed by the rotation of a magnetic bar for 1 minute. Final surfactant concentration in the LR4 emulsion was 2.18% (w/v).

As prepared herein, the LR4 vaccines are stable for at least one year at 5° C.

Using the same preparation method, other emulsions can be obtained as described below:

LR3 Emulsion

First Step:

The final LR3 emulsion is an O/W emulsion containing 33% of an oily phase.

| Oily phase (120 ml): | |
|---|---|
| Oleth-2 (Brij ® 92) | 6.24% w/v, |
| Oleth-10 (Brij ® 96) | 2.76% w/v, |
| Paraffin oil (Marcol 82 ®) | 89.50% v/v, |
| Preservative | 1.50% v/v |

| Aqueous phase #1 (120 ml): | |
|---|---|
| Poloxamer 407 (Lutrol ® F127) | 1.20% w/v, |
| Isotonic buffer containing disodium and monopotassium phosphate 0.02 M (pH 7.8) | Q.S. to 100.0% v/v |

A 5% (w/v) solution of Lutrol® F127 in the same buffer as the vaccine, for example, in disodium and monopotassium phosphate 0.02 M isotonic buffer (pH 7.8) was used to prepare the aqueous phase #1.

When the agitation stopped, the emulsion changed to an oil-in-water emulsion. The emulsion was placed in a cold chamber at 5° C. for at least 4 hours. At this stage, the emulsion was a pre-emulsion containing 50% of oily phase.

Second Step: The aqueous phase #2 (120 ml) is constituted with the isotonic buffer containing disodium and monopotassium phosphate 0.02 M (pH 7.8) and the immunogen(s). The pre-emulsion as prepared in the first step was cooled to about 5° C., diluted by adding half the volume of the aqueous phase #2 at the same temperature, and mixed by the rotation of a magnetic bar for 1 minute. Final surfactant concentration in the LR3 emulsion is 3.40% w/v.

As prepared herein, the LR3 vaccines are stable for at least one year at 5° C.

BE1 emulsion The final BE1 emulsion is an O/W emulsion containing 33% of an oily phase.

| Oily phase (120 ml): | |
| --- | --- |
| Oleth-2 (Brij ® 92) | 3.0% w/v, |
| Oleth-5 (Volpo ® N5) | 9.1% w/v, |
| Paraffin oil (Marcol 82 ®) | 86.4% v/v, |
| Preservative | 1.5% v/v |
| Aqueous phase #1 (240 ml): | |
| Isotonic buffer containing disodium and monopotassium phosphate 0.02 M (pH 7.8) | Q.S. to 100.0% v/v |

The aqueous phase #1 contains isotonic buffer containing disodium and monopotassium phosphate 0.02 M (pH 7.8) 98.5% v/v and the immunogen(s). The BE1 emulsion is not diluted before use. Final surfactant concentration in the BE1 emulsion is 4% w/v.

Example 2

Stability of the Emulsions

The LR4 and LR3 compositions were stable even in presence of concentrated immunogen(s) at 21° C. for at least 9 months. The particle size distribution of the emulsions did not change over this period of time.

Example 3

*Mycoplasma hyopneumoniae* and PCV-2 Combined Vaccine

Composition and Safety in Piglets

Materials and Methods: Two vaccines prepared as described in Example 1, containing either LR3 or LR4 emulsion, 12 Antigen Units of inactivated *Mycoplasma hyopneumoniae* and 2.4 $\log_{10}$ (Antigen Units) of inactivated porcine circovirus type 2/dose. Twenty-four (24) piglets, three weeks old were randomly allocated into two groups. Group 2 of twelve (12) piglets was vaccinated on day 0 with 4 ml of the LR3 vaccine composition by intramuscular route, while the group 3 of twelve (12) piglets was vaccinated on day 0 with 4 ml of the LR4 vaccine composition by intramuscular route. Group 1 corresponds to the unvaccinated control group. The piglets are daily monitored. Two weeks after injection the injection site and the local lesions are observed.

| Treatment | Shock & General Reactions | Hyperthermia ° C. | Relative Average Daily Weight Gain | Size of the Local Reaction (cm³) |
| --- | --- | --- | --- | --- |
| Group 1 (control) | No reaction | −0.1 ± 0.3* | 6.5 ± 1.9 | 0.0 ± 0.0 |
| Group 2 (LR3) | No reaction | 0.6 ± 0.5 | 6.3 ± 1.3 | 1.8 ± 2.8 |
| Group 3 (LR4) | No reaction | 0.1 ± 0.2 | 6.4 ± 1.7 | 8.4 ± 11.4 |

*Mean ± Standard Deviation

Results: LR3 and LR4 adjuvants have shown a good safety profile.

Example 4

Serological Results after Administration of One Dose of a PCV-2 Vaccine Adjuvanted with the LR4 Emulsion Materials and Methods: A vaccine prepared as described in Example 1, containing LR4 emulsion, CpG ODN #2216 50 µg/dose, 1.5 Antigen Unit of inactivated *Mycoplasma hyopneumoniae* and 1.5 $\log_{10}$ (Antigen Units) of inactivated porcine circovirus type 2/dose. Forty (40) piglets, three weeks old and having preexisting high maternal antibodies, were randomly allocated into two groups. Group 2 of twenty (20) piglets was vaccinated on day 0 with 0.5 ml of the LR4 vaccine composition by intradermal route with a needle free injector. Group 1 corresponds to the unvaccinated control group. Blood samples were taken at D0, D21, D41, D63, D84, D126, D153 and D180 post vaccination for titration of the PCV-2 ORF2 antibodies by ELISA.

| Treatment | D0 | D21 | D41 | D63 | D84 | D126 | D153 | D180 |
| --- | --- | --- | --- | --- | --- | --- | --- | --- |
| Group 1 | 3.08 ± 0.58* | 2.57 ± 0.50 | 2.15 ± 0.58 | <1.51 ± 0.48 | <1.51 ± 0.34 | <1.51 ± 0.17 | <1.51 ± 0.05 | <1.51 ± 0.02 |
| Group 2 | 2.91 ± 0.52 | 2.35 ± 0.52 | 2.44 ± 0.35 | 2.67 ± 0.50 | 2.60 ± 0.49 | 2.40 ± 0.49 | 2.48 ± 0.54 | 2.43 ± 0.54 |

*Mean ± Standard Deviation ($\log_{10}$ units)

Results: As demonstrated in the following table, all the vaccinates showed a significant anti-PCV-2 ORF2 antibody response from 7 to 180 days after vaccination even in presence of maternal antibodies at the time of the vaccination.

Example 5

Method of Preparation of *Helicobacter*

Culture: Bacterial cultures were grown from glycerol stocks, using a 5-10% inoculum into Brucella broth supplemented with 10% Fetal Bovine Serum (FBS). Cultures were grown in vented cap flasks in a triple gas incubator (85% $N_2$, 10% $CO_2$, 5% $O_2$) with shaking at about 70 rpm at 37° C. At the time of inoculation, TSA+5% Sheep's Blood (SB) plates were also struck as a diagnostic test to determine sample purity. Colonial morphology was punctiform and clear. Some hemolysis was seen on plates left in the incubator for 3-4 days. Cultures took 24-36 hours to grow to $OD_{600}$>1. Grown cultures were also struck on TSA+5% SB plates, and tested for catalase and urease production (*Helicobacter cerdo* was positive for both).

Centrifugation: Cultures grown to $OD_{600}>1$ were aliquoted into sterile centrifuge bottles and centrifuged at 7500 rpm for 20 minutes with a J10 Beckman rotor at approximately 8600 g. The supernatant was discarded and cell pellets were washed with 1× phosphate-buffered saline (PBS). Pellets were resuspended in PBS and aliquoted into 10-ml vaccine vials, Lyophilization: Antigen preparations was lyophilized for 36 hours with no stabilizers or preservatives. Well-formed cakes were observed.

Pepsin digestion: A pepsin solution (0.1%) was prepared in 10 mM HCl and filter sterilized twice with a 0.2 micron filter. Lyophilized antigen preparation was digested with pepsin (1 μg of pepsin was added for every mg of dried cell mass) for 25 hours at 37° C. and gentle rocking. Samples of 100 μl were spread onto TSA+5% SB plates (incubated at 37° C. in a triple gas microaerophilic incubator) at 18 and 25 hours; no growth was seen after 96 hours, indicating that the pepsin digestion has an inactivation effect.

PBS neutralization: Antigen preparations had a pH of about 2.0 after the pepsin digestion, so they were neutralized with a 2:1 volume of PBS. After pH neutralization, pH was about 7.0.

Example 6

Formulations of Antigen Preparations Prepared from *Helicobacter cerdo* Treated with pepsin or formalin Vaccines will be formulated, as shown in the Table 1, extemporaneously by dissolving the lyophilized bacteria in 10 ml of LR2 adjuvant per vial. Values reflect the concentration of each ingredient after formulation. LR2 emulsion is equivalent to LR4 emulsion described in Example 1. In the LR2 emulsion the final concentration of Lutrol F 127 is 0.20% (w/v) instead of 0.175% (w/v).

TABLE 1

Vaccine Formulations

| Ingredient | Components | Ingredient Quantity mg per ml | Ingredient Quantity mg per dose (2 ml) |
|---|---|---|---|
| PBS | NaCl | 2 | 4 |
|  | KCl | 0.05 | 0.1 |
|  | Na$_2$HPO$_4$ | 0.2875 | 0.575 |
|  | KH$_2$PO$_4$ | 0.05 | 0.1 |
|  | deionized H$_2$O |  |  |
| pepsin (solution) |  | 3.5 μg | 7.0 μg |
|  | HCl | 0.042 | 0.084 |
| *Helicobacter* cells |  | 3.5 | 7.0 |

Example 7

Animals and Methods for Vaccination with *H. cerdo*-based Vaccines

The animals used in this study are selected conventional pigs that are PRRSV-free, and *M. hyopneumoniae*-free. Conventional piglets are selected while still with their mothers. All pigs weights are recorded. The pigs are assigned to 2 groups of at least 5 pigs each, with stratification by weight, sex and litter of origin. All pigs are examined to ensure health status. Only clinically healthy animals are included in the trial. All pigs are identified. Pigs are vaccinated at 1 week and 2 weeks of age while with their mothers. One group of pigs is vaccinated and one group left as unvaccinated control. Vaccinated animals receive 1 dose (2 ml per dose) via the intramuscular route, as 0.5 ml over each shoulder and hip. Unvaccinated controls do not receive any injection.

At 3 weeks of age, all pigs are weaned and challenged. Each group are housed in separate pens in an isolation facility. The pigs are necropsied at approximately 28 days post challenge. The negative control pigs are necropsied at the final necropsy date. The experimental design is summarized in Table 2.

TABLE 2

Experimental Design

| Treatment Description | *Helicobacter* challenge | No challenge |
|---|---|---|
| Vaccinated group | 5 pigs |  |
| Negative Controls |  | 5 pigs |

Challenge Procedure and evaluation. In case of severe clinical illness, treatments that are considered necessary for the animal's welfare may be administered. Each animal's ear tag number, date(s) of illness, presumptive diagnosis, treatment regimen, and disposition of the animal will be recorded. No treatment is provided following challenge. A moribund or injured animal are euthanized. An unhealthy animal (clinical illness or injury) may be withdrawn from the study.

Serology and Skin tests: Blood is collected from the anterior vena cava prior to vaccination, prior to challenge and at necropsy. Helicobacter antibody levels is determined. Skin tests is performed.

Production Parameters: Pigs are weighed upon arrival, prior to vaccination, prior to challenge and at each necropsy to evaluate potential weight gain or loss.

Necropsy: Pigs are necropsied at 28 DPI as adapted to *Helicobacter* challenge.

Example 8

*Helicobacter* Isolates

Two bacterial isolates (2662 and 1268) were recovered from porcine gastric mucosa by micro-aerophilic culture and passageon Skirrow's medium plates.

On the basis of gastric location (cardiac and antrum), morphology (Gram-negative, short, curved "gull wing-like" rods), urease activity, reactivity with a rabbit anti-Hp antibody, both isolates were assigned to the genus Helicobacter based on SDS-PAGE and Western blotting profiles, isolate 2662 was found to be similar to *helicobacter pylori* and given the name "*Helicobacter cerdo*". Isolate 1268 had a distinctive profile unlike that of 2662.

Example 9

Bacterial Load Measured by Urease Activity

TABLE 3

Bacterial Load Measured by Urease Activity

| | Urease Activity in Gastric Mucosa | | | |
|---|---|---|---|---|
| Groups | None | Weak | Moderate | Strong |
| Vaccinated group | 4* | 0 | 2 | — |
| Infection Controls | — | 1 | 3 | 3 |

*Gross lesions pars esophagea

Example 10

Gastric Inflammatory Response

The gastric inflammatory response (Table 4) was "scored" for follicles and lymphocytic infiltrates into the gastric lamina propria on a scale of 0, none; 1, mild; 2, moderate; and 3, severe. The total inflammatory score for each pig was calculated as the sum of the histologic scores in the gastric cardia and antrum. Group mean scores were calculated from these.

TABLE 4

Gastric Inflammatory Response

| Group Number | Mean Total Score |
| --- | --- |
| Vaccinated group | 3.6 |
| Control group | 4.4 |

Example 11

Serological Responses

TABLE 5

Serological responses

| Groups | Day 6 | First Vaccination | Day 14 | Second Vaccination | Day 24 | Day 40 |
| --- | --- | --- | --- | --- | --- | --- |
| Vaccinated group | 1.0 | | 1.3 | | 81.0 | 86.5 |
| Infection Controls | 1.0 | | 0.8 | | 1.3 | 4.5 |
| Suivaxyn Myco hyo + H. cerdo | 6.9 | | 11.8 | | 99.9 | 97.3 |
| Controls | 9.4 | | 6.6 | | 9.1 | 9.0 |

H. cerdo vaccine provided the good indices of protective immunity based upon the intensity of urease activity, blinded histological evaluation of tissue sections and the strong serological responses. A combined vaccine comprising Suivaxyn, *Mycoplasma hyopneumoniae* and *H. cerdo* gave similar antibody responses.

The invention is further described by the following numbered paragraphs:

1. An oil-in-water (O/W) emulsion comprising:
(1) an aqueous solution containing a vaccine antigen or immunogen capable of inducing an immune response in a host;
(2) a non-ionic lipophilic ethoxylated fatty alcohol;
(3) a mineral oil;
(4) a non-ionic hydrophilic surfactant selected from the group of ethoxylated fatty alcohol, polyoxyethylene-polyoxypropylene block copolymer (POE-POP block copolymer) and/or any combination thereof.

2. An oil-in-water (O/W) emulsion comprising:
(1) an aqueous solution containing a vaccine antigen or immunogen capable of inducing an immune response in a host;
(2) a non-ionic lipophilic surfactant selected from the group of ethoxylated fatty alcohol, polyoxyethylene-polyoxypropylene block copolymer (POE-POP block copolymer) and/or any combination thereof;
(3) a mineral oil;
(4) a non-ionic hydrophilic ethoxylated fatty alcohol.

3. The emulsion of paragraph 1 or 2 wherein the lipophilic ethoxylated fatty alcohol comprises about 43% of the molecular weight (w/w) or less of ethylene oxide (EO).

4. The emulsion of paragraph 2 wherein the lipophilic POE-POP block copolymer comprises about 35% (w/w) or less of ethylene oxide.

5. The emulsion of paragraph 2 wherein the hydrophilic ethoxylated fatty alcohol comprises more than about 43% (w/w) of ethylene oxide (EO).

6. The emulsion of paragraph 1 wherein the hydrophilic POE-POP block copolymer comprises about 55% (w/w) or more of ethylene oxide.

7. The emulsion of paragraph 3 wherein the ethoxylated fatty alcohol is a C9 to C22 fatty alcohol and advantageously selected from the group consisting of an oleyl, cetyl, stearyl, isostearyl, lauryl alcohol, and combinations thereof, advantageously an oleyl alcohol and more advantageously an ethoxylated oleyl alcohol with 1 to 4 EO.

8. The emulsion of paragraph 5 wherein the ethoxylated fatty alcohol is a C9 to C22 fatty alcohol and advantageously selected from the group consisting of an oleyl, cetyl, stearyl, isostearyl, lauryl alcohol, and combinations thereof, advantageously an oleyl alcohol and more advantageously an ethoxylated oleyl alcohol with 5 to 21 EO.

9. The emulsion of paragraph 4 wherein the POE-POP block copolymer has a MW of about 1000 to about 8000.

10. The emulsion of paragraph 6 wherein the POE-POP block copolymer has a MW of about 3000 to about 16000.

11. The emulsion of any one of paragraphs 1 to 10, wherein the non-ionic hydrophilic surfactant is an ethoxylated fatty alcohol.

12. The emulsion of paragraph 11 wherein the ethoxylated fatty alcohol is Brij® 76, Brij® 56, Brij® 96/97, Brij® 98, Brij® 721, Brij® 58, Brij® 35, Brij® 78 (Uniqema), Volpo® N5, Volpo® CS6, Volpo® CS 12, Volpo® CS20, Volpo® CS25, Volpo® CS23 (Croda), BL9-EX, BC-7, BT-5, BT-7, BT-9, BT-12, BD-10, BO-7V, BC5.5, BT-5, BL-21, BL-25, BC-15TX, BC-23, BC-25TX, BO-15V, BO-50V, BB-20, (Nikko Chemicals) or any combination thereof.

13. The emulsion of any one of paragraphs 1 to 12, wherein the non-ionic hydrophilic surfactant is a POE-POP block copolymer.

14. The emulsion of paragraph 13 wherein the POE-POP block copolymer is Lutrol® F127 [Poloxamer 407], Lutrol® F68 [Poloxamer 188], Lutrol® F108 [Poloxamer 338], Lutrol® F98 [Poloxamer 278], Lutrol®F87 [Poloxamer 227], Lutrol® F88 [ Poloxamer 228], Lutrol® F77 [ Poloxamer 207], Lutrol® F38 [ Poloxamer 108] (BASF), Tetronics®T1307, Tetronics®T1107, Tetronics®T908 (BASF) or any combination thereof.

15. The emulsion of any one of paragraphs 1 to 14, wherein the non-ionic lipophilic surfactant is an ethoxylated fatty alcohol.

16. The emulsion of paragraph 15 wherein the ethoxylated fatty alcohol is Brij® 30, Brij® 92/93, Brij® 72, Brij® 52 (Uniqema), Volpo® L3, Volpo® N3, Volpo® L4 (Croda), BS-4, BD-2, BD-4, BT-3 (Nikko Chemicals) or any composition thereof.

17. The emulsion of any one of paragraphs 1 to 16 wherein the non-ionic lipophilic surfactant is a POE-POP block copolymer.

18. The emulsion of paragraph 17 wherein the POE-POP block copolymer is Pluronic® L121 [Poloxamer 401], Pluronic® L101 [Poloxamer 331], Pluronic® L81 [Poloxamer 221], Pluronic® L62 [Poloxamer 182], Pluronic® L43 [Poloxamer 123], Pluronic® P103 [Poloxamer 333], Pluronic® L123 [Poloxamer 403], Lutrol® L63 [ Poloxamer 183], Lutrol® P122 [Poloxamer 402], Lutrol® L92 [Poloxamer 272], Lutrol® L72 [Poloxamer 202], Lutrol® L42 [Poloxamer 122], Lutrol® L61 [Poloxamer 181] (BASF), Tetronics®T1301, Tetronics® T701, Tetronics®T901 (BASF) or any combination thereof.

19. The emulsion of any one of paragraphs 1 to 18 wherein the overall concentration of surfactants, by weight per volume of emulsion is from about 0.2% to about 6.5%, in particular from about 1% to about 6%, advantageously from about 1.5% to about 5%, more advantageously from about 2% to about 3%.

20. An oil-in-water (O/W) emulsion comprising:
   (1) an aqueous solution containing a vaccine antigen or immunogen capable of inducing an immune response in a host;
   (2) a non-ionic lipophilic ethoxylated fatty alcohol;
   (3) a mineral oil;
   (4) a non-ionic hydrophilic ethoxylated fatty alcohol comprising more than about 43% and less than about 71% (w/w) of ethylene oxide (EO);
   (5) a non-ionic hydrophilic ethoxylated fatty alcohol comprising about 71% or more (w/w) of ethylene oxide (EO).

21. The emulsion of paragraph 20 wherein the non-ionic hydrophilic ethoxylated fatty alcohol comprising more than about 43% and less than about 71% (w/w) of ethylene oxide (EO) is an ethoxylated oleyl alcohol with 5 to 14 EO.

22. The emulsion of paragraph 20 or 21 wherein the non-ionic hydrophilic ethoxylated fatty alcohol comprising about 71% or more (w/w) of ethylene oxide (EO) is an ethoxylated oleyl alcohol with 15 EO or more.

23. The emulsion of any one of paragraphs 20 to 22 wherein the concentration of the non-ionic hydrophilic ethoxylated fatty alcohol comprising more than about 43% and less than about 71% (w/w) of ethylene oxide is from about 1.0% to about 5.0%, in particular from about 1.5% to about 4.5%, more advantageously from about 2.0% to about 3.5%, expressed as a percentage in weight by volume of emulsion (w/v).

24. The emulsion of any one of paragraphs 20 to 23 wherein the concentration of non-ionic hydrophilic ethoxylated fatty alcohol comprising about 71% or more (w/w) of ethylene oxide is from about 0.01% to about 3.0%, particularly from about 0.05% to about 2.5%, more advantageously from about 0.1% to about 2.0% (w/v).

25. The emulsion of any one of paragraphs 20 to 24 wherein the concentration of the non-ionic lipophilic ethoxylated fatty alcohol is from about 0.1% to about 2.5%, in particular from about 0.2% to about 2.0%, advantageously from about 0.2% to about 1.5%, more advantageously from about 0.2% to about 1.2% (w/v).

26. An oil-in-water (O/W) emulsion comprising:
   (1) an aqueous solution containing a vaccine antigen or immunogen capable of inducing an immune response in a host;
   (2) a non-ionic lipophilic ethoxylated fatty alcohol;
   (3) a mineral oil;
   (4) a non-ionic hydrophilic ethoxylated fatty alcohol;
   (5) a non-ionic hydrophilic polyoxyethylene-polyoxypropylene block copolymer.

27. The emulsion of paragraph 26 wherein the hydrophilic ethoxylated fatty alcohol is advantageously an ethoxylated fatty alcohol comprising more than about 43% and less than about 71% (w/w) of ethylene oxide.

28. The emulsion of paragraph 27 wherein the fatty alcohol is an ethoxylated oleyl alcohol with 5 to 14 EO.

29. The emulsion of any one of paragraphs 26 to 28 wherein the concentration of non-ionic hydrophilic ethoxylated fatty alcohol is from about 1.0% to about 5.0%, in particular from about 1.5% to about 4.5%, more advantageously from about 2.0% to about 3.5%, expressed as a percentage in weight by volume of emulsion (w/v).

30. The emulsion of any one of paragraphs 26 to 29 wherein the concentration of the non-ionic hydrophilic polyoxyethylene-polyoxypropylene block-copolymer is from about 0.01% to about 2.0%, more particularly from about 0.1% to about 1.5% (w/v).

31. The emulsion of any one of paragraphs 26 to 30 wherein the concentration of the non-ionic lipophilic ethoxylated fatty alcohol is from about 0.1% to about 2.5%, in particular from about 0.2% to about 2.0%, advantageously from about 0.2% to about 1.5%, more advantageously from about 0.2% to about 1.2% (w/v).

32. The emulsion of any one of paragraphs 1 to 31 wherein the emulsion has a phase inversion temperature (PIT) greater than or equal to 25° C.

33. The emulsion of paragraph 32 wherein the PIT is from about 28° C. to about 65° C., more particularly from about 33° C. to about 60° C.

34. The emulsion of any one of paragraphs 1 to 33 wherein the emulsion comprises by volume per volume (v/v) of emulsion, from about 2% to about 50% of oil phase including the oil(s) and the surfactants, in particular from about 4% to about 40%, advantageously from about 8% to about 35% and, more advantageously, from about 15% to about 30% of oil phase.

35. The emulsion of paragraph 34 wherein the oil is a mineral oil.

36. The emulsion of paragraph 35 wherein the mineral oil is a paraffin oil such as isoparaffinic oil and/or naphthenic oil, squalane, squalene, pristane, polyisobutene, hydrogenated polyisobutene, polydecene, polyisoprene, polyisopropene and the like.

37. The emulsion of paragraph 34 or 35 wherein the mineral oil comprises a linear or ramified carbon chain having a number of carbon atoms greater than 15, advantageously from 15 to 32, and free of aromatic compounds.

38. The emulsion of paragraph 37 wherein the oil is marketed under the name MARCOL® 52 or MARCOL® 82 (Esso,) or "DRAKEOL® 6VR" (Penreco,).

39. The emulsion of any one of paragraphs 34 to 38 wherein the oil is a mixture of oils comprising at least two oils in any proportion.

40. The emulsion of paragraph 39 wherein the mixture of oils comprises at least one vegetable oil.

41. The emulsion of paragraph 40 wherein the vegetable oil represents from about 0.1% to about 33% of the oily phase, advantageously from about 5% to about 15% v/v.

42. The emulsion of paragraph 40 or 41 wherein the vegetable oil is groundnut oil, nut oil, sunflower oil, safflower oil, soya oil, evening primrose oil and the like.

43. An emulsion comprising a paraffin oil; an ethoxylated oleyl alcohol with 2-3 EO as non-ionic lipophilic surfactant; an ethoxylated oleyl alcohol with 5-6 EO as non-ionic hydrophilic surfactant; and a POE-POP block copolymer with approximately 70 to 80% EO and a MW around 9800 to 16000 as non-ionic hydrophilic surfactant.

44. The emulsion of paragraph 43 wherein the paraffin oil is at a concentration from about 5% about 50% and advantageously from about 15% to about 30% (v/v); the ethoxylated oleyl alcohol with 2-3 EO is at the concentration from 0.1% to 1.5%, advantageously from 0.1% to 1.2% (w/v); the ethoxylated oleyl alcohol with 5-6 EO is at the concentration from 1% to 5%, advantageously from 1% to 4% (w/v); and the POE-POP block copolymer with approximately 70 to 80%

EO and a MW around 9800 to 16000 is at the concentration from 0.01% to 2%, advantageously from 0.05% to 1.5% (w/v).

45. An emulsion comprising a paraffin oil, an ethoxylated oleyl alcohol with 2-3 EO as non-ionic lipophilic surfactant; an ethoxylated oleyl alcohol with 10 OE as non-ionic hydrophilic surfactant; and a POE-POP block copolymer with approximately 70 to 80% EO and a MW around 9800 to 16000 as non-ionic hydrophilic surfactant.

46. The emulsion of paragraph 45 wherein the paraffin oil is at a concentration from 5% to 50%, advantageously from 15% to 30% (v/v); the ethoxylated oleyl alcohol with 2-3 EO is at the concentration from 0.2% to 3%, advantageously from 0.5% to 3% (w/v); the ethoxylated oleyl alcohol with 10 EO is at the concentration from 0.2% to 3%, advantageously from 0.5% to 3% (w/v); and the POE-POP block copolymer with approximately 70 to 80% EO and a MW around 9800 to 16000 is at the concentration from 0.01% to 2%, advantageously from 0.05% to 1.5% (w/v).

47. An emulsion comprising a paraffin oil, an ethoxylated oleyl alcohol with 2-3 EO as non-ionic lipophilic surfactant and an ethoxylated oleyl alcohol with 5-6 OE as non-ionic hydrophilic surfactant.

48. The emulsion of paragraph 47 wherein the paraffin oil is at a concentration from 5% to 50%, advantageously from 15% to 35% (v/v); the ethoxylated oleyl alcohol with 2-3 EO is at the concentration from 0.1% to 3%, advantageously from 0.5% to 2% (w/v); the ethoxylated oleyl alcohol with 5-6 EO is at the concentration from 1% to 5%, advantageously from 2.0% to 4.5% (w/v).

49. A method of making a vaccine composition comprising mixing a vaccine antigen or immunogen capable of inducing an immune response in a host with an emulsion of any one of paragraphs 1 to 48.

50. A method for inducing an immune response in a host comprising administering the emulsion of any one of paragraphs 1 to 48 or the vaccine composition of paragraph 49 to the host.

51. A kit for performing the method of paragraph 49 or 50 comprising the emulsion of any one of paragraphs 1 to 48 or the vaccine composition of paragraph 49 and instructions for performing the method.

Having thus described in detail advantageous embodiments of the present invention, it is to be understood that the invention defined by the above paragraphs is not to be limited to particular details set forth in the above description as many apparent variations thereof are possible without departing from the spirit or scope of the present invention.

What is claimed is:

1. An oil-in-water (O/W) emulsion comprising:
   (1) an aqueous solution containing a vaccine antigen or immunogen capable of inducing an immune response in a host, wherein the antigen or immunogen is a whole organism, a killed organism, an attenuated organism, a live organism, a recombinant vector containing an insert with immunogenic properties, a piece or fragment of DNA capable of inducing an immune response upon presentation to a host animal, a protein, a glycoprotein, a lipoprotein, a polypeptide, a peptide, a toxin or an antitoxin;
   (2) a non-ionic lipophilic ethoxylated fatty alcohol;
   (3) a mineral oil;
   (4) a non-ionic hydrophilic surfactant selected from the group of ethoxylated fatty alcohol, polyoxyethylene-polyoxypropylene block copolymer (POE-POP block copolymer) and/or any combination thereof.

2. An oil-in-water (O/W) emulsion comprising:
   (1) an aqueous solution containing a vaccine antigen or immunogen capable of inducing an immune response in a host, wherein the antigen or immunogen is a whole organism, a killed organism, an attenuated organism, a live organism, a recombinant vector containing an insert with immunogenic properties, a piece or fragment of DNA capable of inducing an immune response upon presentation to a host animal, a protein;
   (2) a non-ionic lipophilic surfactant selected from the group of ethoxylated fatty alcohol, polyoxyethylene-polyoxypropylene block copolymer (POE-POP block copolymer) and/or any combination thereof;
   (3) a mineral oil;
   (4) a non-ionic hydrophilic ethoxylated fatty alcohol.

3. The emulsion of claim 1 wherein the lipophilic ethoxylated fatty alcohol comprises about 43% of the molecular weight (w/w) or less of ethylene oxide (EO) or
   wherein the hydrophilic POE-POP block copolymer comprises about 55% (w/w) or more of ethylene oxide or
   wherein the lipophilic ethoxylated fatty alcohol comprises about 43% of the molecular weight (w/w) or less of ethylene oxide (EO) and
   wherein the ethoxylated fatty alcohol is a C9 to C22 fatty alcohol or
   wherein the hydrophilic POE-POP block copolymer comprises about 55% (w/w) or more of ethylene oxide and
   wherein the POE-POP block copolymer has a MW of about 3000 to about 16000 or
   wherein the non-ionic hydrophilic surfactant is an ethoxylated fatty alcohol or
   wherein the hydrophilic ethoxylated fatty alcohol comprises more than about 43% (w/w) of ethylene oxide or
   wherein the hydrophilic ethoxylated fatty alcohol comprises more than about 43% (w/w) of ethylene oxide and wherein the ethoxylated fatty alcohol is a C9 to C22 fatty alcohol or
   wherein the non-ionic hydrophilic surfactant is an ethoxylated fatty alcohol and
   wherein the ethoxylated fatty alcohol is Steareth-10, Ceteth-10, Oleth-10, Oleth-20, Steareth-21, Ceteth-20, Laureth-23, Steareth-20, Oleth-5, Ceteareth-6, Ceteareth-12, Ceteareth-20, Ceteareth-25, Ceteareth-23, Laureth-9, Ceteth-7, C12-14 Pareth-5, C12-14 Pareth-7, C12-14 Pareth-9, C12-14 Pareth-12, C12-15 Pareth-10, Oleth-7, Ceteht-6, Laureth-21, Laureth-25, Ceteth-15, Ceteth-23, Ceteth-25, Oleth-15, Oleth-50, Beheneth-20, or any combination thereof or
   wherein the non-ionic hydrophilic surfactant is a POE-POP block copolymer or
   wherein the non-ionic hydrophilic surfactant is a POE-POP block copolymer and
   wherein the POE-POP block copolymer is Poloxamer 407, Poloxamer 188, Poloxamer 338, Poloxamer278, Poloxamer 227, Poloxamer 228, Poloxamer 207, Poloxamer 108, a poloxamine 1307, poloxamine 1107, poloxamine 908 or any combination thereof or
   wherein the non-ionic lipophilic surfactant is an ethoxylated fatty alcohol or
   wherein the non-ionic lipophilic surfactant is an ethoxylated fatty alcohol and
   wherein the ethoxylated fatty alcohol is Laureth-4, Oleth-2, Steareth-2, Ceteth-2, C12-13 Pareth-3, Oleth-3, C12-13 Pareth-4, Steareth-4, C12-15 Pareth-2, C12-15 Pareth-4, C12-14 Pareth-3 or any composition thereof or
   wherein the overall concentration of surfactants, by weight per volume of emulsion is from about 0.2% to about 6.5.

4. The emulsion of claim 2 wherein the lipophilic ethoxylated fatty alcohol comprises about 43% of the molecular weight (w/w) or less of ethylene oxide (EO) or
- wherein the lipophilic POE-POP block copolymer comprises about 35% (w/w) or less of ethylene oxide or
- wherein the hydrophilic ethoxylated fatty alcohol comprises more than about 43% (w/w) of ethylene oxide (EO) or
- wherein the lipophilic ethoxylated fatty alcohol comprises about 43% of the molecular weight (w/w) or less of ethylene oxide (EO) and
- wherein the ethoxylated fatty alcohol is a C9 to C22 fatty alcohol or
- wherein the hydrophilic ethoxylated fatty alcohol comprises more than about 43% (w/w) of ethylene oxide (EO) and
- wherein the ethoxylated fatty alcohol is a C9 to C22 fatty alcohol or
- wherein the lipophilic POE-POP block copolymer comprises about 35% (w/w) or less of ethylene oxide and
- wherein the POE-POP block copolymer has a MW of about 1000 to about 8000 or
- wherein the non-ionic hydrophilic surfactant is an ethoxylated fatty alcohol or
- wherein the non-ionic hydrophilic surfactant is an ethoxylated fatty alcohol and
- wherein the ethoxylated fatty alcohol is Steareth-10, Ceteth-10, Oleth-10, Oleth-20, Steareth-21, Ceteth-20, Laureth-23, Steareth-20, Oleth-5, Ceteareth-6, Ceteareth-12, Ceteareth-20, Ceteareth-25, Ceteareth-23, Laureth-9, Ceteth-7, C12-14 Pareth-5, C12-14 Pareth-7, C12-14 Pareth-9, C12-14 Pareth-12, C12-15 Pareth-10, Oleth-7, Ceteht-6, Laureth-21, Laureth-25, Ceteth-15, Ceteth-23, Ceteth-25, Oleth-15, Oleth-50, Beheneth-20, or any combination thereof or
- wherein the non-ionic lipophilic surfactant is an ethoxylated fatty alcohol or
- wherein the non-ionic lipophilic surfactant is an ethoxylated fatty alcohol and
- wherein the ethoxylated fatty alcohol is Laureth-4, Oleth-2, Steareth-2, Ceteth-2, C12-13 Pareth-3, Oleth-3, 4 C12-13 Pareth-4, Steareth-4, C12-15 Pareth-2, C12-15 Pareth-4, C12-14 Pareth-3 or any composition thereof or
- wherein the non-ionic lipophilic surfactant is a POE-POP block copolymer or
- wherein the non-ionic lipophilic surfactant is a POE-POP block copolymer and
- wherein the POE-POP block copolymer is Poloxamer 401, Poloxamer 331, Poloxamer 221, Poloxamer 182, Poloxamer 123, Poloxamer 333, Poloxamer 403, Poloxamer 183, Poloxamer 402, Poloxamer 272, Poloxamer 202, Poloxamer 122, Poloxamer 181, poloxamine 1307, poloxamine 1107, poloxamine 908 or any combination thereof or
- wherein the overall concentration of surfactants, by weight per volume of emulsion is from about 0.2% to about 6.5%.

5. The emulsion of claim 1 wherein the non-ionic hydrophilic surfactant comprises a non-ionic hydrophilic ethoxylated fatty alcohol comprising more than about 43% and less than about 71% (w/w) of ethylene oxide (EO) and a non-ionic hydrophilic ethoxylated fatty alcohol comprising about 71% or more (w/w) of ethylene oxide (EO).

6. The emulsion of claim 5 wherein the non-ionic hydrophilic ethoxylated fatty alcohol comprising more than about 43% and less than about 71% (w/w) of ethylene oxide (EO) is an ethoxylated oleyl alcohol with 5 to 14 EO or
- wherein the non-ionic hydrophilic ethoxylated fatty alcohol comprising about 71% or more (w/w) of ethylene oxide (EO) is an ethoxylated oleyl alcohol with 15 EO or more or
- wherein the concentration of the non-ionic hydrophilic ethoxylated fatty alcohol comprising more than about 43% and less than about 71% (w/w) of ethylene oxide is from about 1.0% to about 5.0% expressed as a percentage in weight by volume of emulsion (w/v) or
- wherein the concentration of non-ionic hydrophilic ethoxylated fatty alcohol comprising about 71% or more (w/w) of ethylene oxide is from about 0.01% to about 3.0% or
- wherein the concentration of the non-ionic lipophilic ethoxylated fatty alcohol is from about 0.1% to about 2.5%.

7. The emulsion of claim 1 wherein the non-ionic hydrophilic surfactant comprises a non-ionic hydrophilic ethoxylated fatty alcohol and a non-ionic hydrophilic polyoxyethylenepolyoxypropylene block copolymer.

8. The emulsion of claim 7 wherein the hydrophilic ethoxylated fatty alcohol is an ethoxylated fatty alcohol comprising more than about 43% and less than about 71% (w/w) of ethylene oxide or
- wherein the fatty alcohol is an ethoxylated oleyl alcohol with 5 to 14 EO or
- wherein the concentration of non-ionic hydrophilic ethoxylated fatty alcohol is from about 1.0% to about 5.0% expressed as a percentage in weight by volume of emulsion (w/v) or
- wherein the concentration of the non-ionic hydrophilic polyoxyethylenepolyoxypropylene block-copolymer is from about 0.01% to about 2.0% (w/v) or
- wherein the concentration of the non-ionic lipophilic ethoxylated fatty alcohol is from about 0.1% to about 2.5% (w/v).

9. The emulsion of claim 1 wherein the emulsion has a phase inversion temperature (PIT) greater than or equal to 25° C. or
- wherein the emulsion has a phase inversion temperature (PIT) greater than or equal to 25° C. and
- wherein the PIT is from about 28° C. to about 65° C.

10. The emulsion of claim 1 wherein the emulsion comprises by volume per volume (v/v) of emulsion, from about 2% to about 50% of oil phase including the oil(s) and the surfactants or
- wherein the emulsion comprises by volume per volume (v/v) of emulsion, from about 2% to about 50% of oil phase including the oil(s) and the surfactants and
- wherein the oil is a mineral oil or
- wherein the emulsion comprises by volume per volume (v/v) of emulsion, from about 2% to about 50% of oil phase including the oil(s) and the surfactants and
- wherein the oil is a mineral oil and
- wherein the mineral oil is a paraffin oil, isoparaffinic oil, naphthenic oil, squalane, squalene, pristane, polyisobutene, hydrogenated polyisobutene, polydecene, polyisoprene, polyisopropene or
- wherein the emulsion comprises by volume per volume (v/v) of emulsion, from about 2% to about 50% of oil phase including the oil(s) and the surfactants and
- wherein the oil is a mineral oil and
- wherein the mineral oil comprises a linear or ramified carbon chain having a number of carbon atoms greater than 15 or wherein the emulsion comprises by volume per volume (v/v) of emulsion, from about 2% to about 50% of oil phase including the oil(s) and the surfactants and wherein the oil is a mineral oil and wherein the mineral oil comprises a linear or ramified carbon chain having a number of carbon atoms greater than 15 and free of aromatic compounds or wherein the oil is a mixture of oils comprising at least two oils in any proportion or wherein the oil is a mixture of oils comprising at least two oils in any proportion and wherein the mixture of oils comprises at least one vegetable oil or wherein the oil is a mixture of oils comprising at least two oils in any proportion and wherein the mixture of oils comprises at least one vegetable oil and wherein the vegetable oil represents from about 0.1% to about 33% v/v of the oily phase wherein the oil is a mixture of oils comprising at least two oils in any proportion and wherein the mixture of oils comprises at least one vegetable oil and wherein the vegetable oil is groundnut oil, nut oil, sunflower oil, safflower oil, soya oil, evening primrose oil.

11. The emulsion of claim 2 wherein the emulsion has a phase inversion temperature (PIT) greater than or equal to 25° C. or wherein the emulsion has a phase inversion temperature (PIT) greater than or equal to 25° C. and wherein the PIT is from about 28° C. to about 65° C.

12. The emulsion of claim 2 wherein the emulsion comprises by volume per volume (v/v) of emulsion, from about 2% to about 50% of oil phase including the oil(s) and the surfactants or wherein the emulsion comprises by volume per volume (v/v) of emulsion, from about 2% to about 50% of oil phase including the oil(s) and the surfactants and wherein the oil is a mineral oil or wherein the emulsion comprises by volume per volume (v/v) of emulsion, from about 2% to about 50% of oil phase including the oil(s) and the surfactants and wherein the oil is a mineral oil and wherein the mineral oil is a paraffin oil, isoparaffinic oil, naphthenic oil, squalane, squalene, pristane, polyisobutene, hydrogenated polyisobutene, polydecene, polyisoprene, polyisopropene or wherein the emulsion comprises by volume per volume (v/v) of emulsion, from about 2% to about 50% of oil phase including the oil(s) and the surfactants and wherein the oil is a mineral oil and wherein the mineral oil comprises a linear or ramified carbon chain having a number of carbon atoms greater than 15 and free of aromatic compounds or wherein the emulsion comprises by volume per volume (v/v) of emulsion, from about 2% to about 50% of oil phase including the oil(s) and the surfactants and wherein the oil is a mineral oil and wherein the mineral oil comprises a linear or ramified carbon chain having a number of carbon atoms greater than 15 and free of aromatic compounds or wherein the oil is a mixture of oils comprising at least two oils in any proportion or wherein the oil is a mixture of oils comprising at least two oils in any proportion and wherein the mixture of oils comprises at least one vegetable oil or wherein the oil is a mixture of oils comprising at least two oils in any proportion and wherein the mixture of oils comprises at least one vegetable oil and wherein the vegetable oil represents from about 0.1% to about 33% of the oily phase v/v.

wherein the oil is a mixture of oils comprising at least two oils in any proportion and wherein the mixture of oils comprises at least one vegetable oil and wherein the vegetable oil is groundnut oil, nut oil, sunflower oil, safflower oil, soya oil, evening primrose oil.

13. The emulsion of claim 1 wherein the vaccine antigen or immunogen is *Mycoplasma hyopneumoniae*, porcine circovirus 2 or *Helicobacter pylori*.

14. The emulsion of claim 2 wherein the vaccine antigen or immunogen is *Mycoplasma hyopneumoniae*, porcine circovirus 2 or *Helicobacter pylori*.

15. An emulsion comprising a paraffin oil, an ethoxylated oleyl alcohol with 2-3 EO as non-ionic lipophilic surfactant; an ethoxylated oleyl alcohol with 10 OE as non-ionic hydrophilic surfactant; and a POE-POP block copolymer with approximately 70 to 80% EO and a MW around 9800 to 16000 as non-ionic hydrophilic surfactant.

16. The emulsion of claim 15 wherein the paraffin oil is at a concentration from 5% to 50%; the ethoxylated oleyl alcohol with 2-3 EO is at the concentration from 0.2% to 3%; the ethoxylated oleyl alcohol with 10 EO is at the concentration from 0.2% to 3%; and the POE-POP block copolymer with approximately 70 to 80% EO and a MW around 9800 to 16000 is at the concentration from 0.01% to 2%.

17. An emulsion comprising a paraffin oil, an ethoxylated oleyl alcohol with 2-3 EO as non-ionic lipophilic surfactant and an ethoxylated oleyl alcohol with 5-6 OE as non-ionic hydrophilic surfactant.

18. The emulsion of claim 17 wherein the paraffin oil is at a concentration from 5% to 50%; the ethoxylated oleyl alcohol with 2-3 EO is at the concentration from 0.1% to 3%; the ethoxylated oleyl alcohol with 5-6 EO is at the concentration from 1% to 5%.

19. A composition comprising the emulsion of claim 15 and a vaccine antigen or immunogen, wherein the vaccine antigen or immunogen is *Mycoplasma hyopneumoniae*, porcine circovirus 2 or *Helicobacter pylori*.

20. A composition comprising the emulsion of claim 17 and a vaccine antigen or immunogen, wherein the vaccine antigen or immunogen is *Mycoplasma hyopneumoniae*, porcine circovirus 2 or *Helicobacter pylori*.

* * * * *